United States Patent

Karrer

[11] Patent Number: 5,114,968
[45] Date of Patent: May 19, 1992

[54] ACYLATED CARBAMATES AND USE AS INSECTICIDES

[75] Inventor: Friedrich Karrer, Zofingen, Switzerland

[73] Assignee: Ciba-Geigy Corporation, Ardsley, N.Y.

[21] Appl. No.: 510,493

[22] Filed: Apr. 18, 1990

[30] Foreign Application Priority Data

Apr. 24, 1989 [CH] Switzerland .................. 1557/89

[51] Int. Cl.⁵ ............... A61K 31/27; C07D 269/02
[52] U.S. Cl. ........................... 514/482; 514/486; 560/26; 560/27
[58] Field of Search ........... 514/486, 482; 560/27, 560/26

[56] References Cited

U.S. PATENT DOCUMENTS

| | | | |
|---|---|---|---|
| 4,080,470 | 3/1990 | Karrer | 424/300 |
| 4,215,139 | 7/1990 | Fischer | 424/300 |
| 4,413,010 | 11/1983 | Zurfluh | 424/300 |
| 4,555,405 | 11/1985 | Boger | 514/488 |
| 4,608,389 | 8/1986 | Kisida | 514/539 |
| 4,745,128 | 5/1988 | Ujvari | 514/483 |

FOREIGN PATENT DOCUMENTS 3320534 12/1983 Fed. Rep. of Germany.
3334983 4/1984 Fed. Rep. of Germany.

*Primary Examiner*—Johann Richter
*Attorney, Agent, or Firm*—Kevin T. Mansfield; Edward McC. Roberts

[57] ABSTRACT

Novel N-acylated 2-[4-(4-fluorophenoxy)phenoxy]ethylcarmabates of formula I

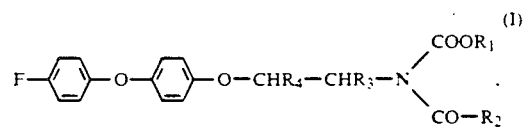

wherein $R_1$ is $C_1$-$C_8$alkyl, $C_3$-$C_4$alkenyl or $C_3$-$C_4$alkynyl, $R_2$ is $C_1$-$C_8$alkyl, $C_1$-$C_8$alkoxy, —CO—$R_5$ or —$NR_6R_7$, $R_3$ and $R_4$ are each independently of the other hydrogen or methyl, $R_5$ is $C_1$-$C_8$alkoxy or —$NR_8R_9$, $R_6$ is $C_1$-$C_4$alkyl, $R_7$ is $C_1$-$C_4$alkyl or $R_6$ and $R_7$ together are a $C_4$-$C_6$alkylene chain which may be interrupted by oxygen, sulfur or —$NCH_3$—, $R_8$ is hydrogen or $C_1$-$C_4$alkyl, and $R_9$ is hydrogen, $C_1$-$C_4$alkyl, benzyl, phenyl or phenyl which is substituted by halogen or methyl, or $R_8$ and $R_9$ together are a $C_4$-$C_6$alkylene chain which may be interrupted by oxygen, sulfur or —$NCH_3$—.

9 Claims, No Drawings

ACYLATED CARBAMATES AND USE AS INSECTICIDES

The present invention relates to novel acylated 2-[4-(4-fluorophenoxy)phenoxy]ethylcarbamates, to their preparation and to the use thereof in pest control, as well as to pesticidal compositions which contain said carbamates as active components.

The N-acyl-2-[4-(4-fluorophenoxy)phenoxy]ethylcarbamates of this invention have the formula I

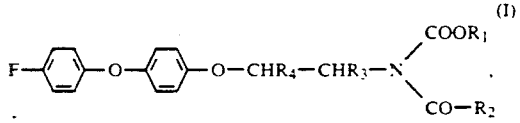

wherein
- $R_1$ is $C_1-C_8$alkyl, $C_3-C_4$alkenyl or $C_3-C_4$alkynyl,
- $R_2$ is $C_1-C_8$alkyl, $C_1-C_8$alkoxy, $-CO-R_5$ or $-NR_6R_7$,
- $R_3$ and $R_4$ are each independently of the other hydrogen or methyl,
- $R_5$ is $C_1-C_8$alkoxy or $-NR_8R_9$,
- $R_6$ is $C_1-C_4$alkyl,
- $R_7$ is $C_1-C_4$alkyl or
- $R_6$ and $R_7$ together are a $C_4-C_6$alkylene chain which may be interrupted by oxygen, sulfur or $-NCH_3-$,
- $R_8$ is hydrogen or $C_1-C_4$alkyl, and
- $R_9$ is hydrogen, $C_1-C_4$alkyl, benzyl, phenyl or phenyl which is substituted by halogen or methyl, or
- $R_8$ and $R_9$ together are a $C_4-C_6$alkylene chain which may be interrupted by oxygen, sulfur or $-NCH_3-$.

Halogen in the definition of $R_9$ will be understood as meaning fluoro, chloro, bromo or iodo, but is preferably chloro.

$C_1-C_8$Alkyl groups may be straight-chain or branched. Such radicals are, typically, methyl, ethyl, propyl, isopropyl or butyl and its isomers as well as the possible structural isomers of the $C_5-C_8$alkyl groups. Preferred alkyl groups contain not more than 4 carbon atoms. Methyl and ethyl are especially preferred.

Within the scope of this invention, $C_1-C_8$alkoxy groups in the definition of $R_2$ and $R_5$ are methoxy, ethoxy, propoxy, isopropoxy or the four isomers of butoxy or the possible structural isomers of the $C_5-C_8$alkoxy groups. To be singled oput for special mention are the short-chain alkoxy groups containing fewer than 5 carbon atoms. Among these groups, methoxy and ethoxy are preferred.

If $R_6$ and $R_7$, or $R_8$ and $R_9$, together form a $C_4-C_6$alkylene chain which may be interrupted by oxygen, sulfur or $-NCH_3-$, the groups $-NR_6R_7$ or $-NR_8R_9$ form a heterocycle which is bound through the nitrogen atom. These heterocycles have, typically, the basic structures of pyrrolidine, piperidine, perhydroazepine, oxazolidine, thiazolidine, imidazolidine, pyrazolidine, perhydropyrimidine, morpholine, thiomorpholine, perhydropyridazine, isoxazolidine, isothiazolidine or piperazine.

Various pesticidal ethylcarbamate derivatives are known from the literature, but the activity spectrum achieved with these compounds is unsatisfactory or only partially satisfactory. Such compounds are disclosed, for example, in U.S. Pat. Nos. 4,080,470; 4,215,139, 4,413,010; 4,555,405; 4,608,389 and 4,745,128, as well as German Offenlegungsschrift specifications 3 320 534 und 3 334 983. Hence there is still a need for pesticides of this class of compounds with improved properties.

It has now been found that the compounds of formula I of this invention are useful compounds in pest control and are well tolerated by warm-blooded animals, fish and plants. The compounds of this invention are applied especially against insects and arachnids which are pests in crop plants and ornamentals in agriculture, especially in cotton, vegetable and fruit crops, in forestry, in the storage and protection sectors and in the hygiene sector, especially pests of domestic animals and productive livestock. The compounds of formula I are effective against all or individual development stages of normal sensitive and also resistant species. Their activity may be observed in an immediate kill of the pests or not until after a time lapse, for example in moulting, or in diminished oviposition and/or hatching rate. The above mentioned pests include: of the order of the Lepidoptera, for example Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp:, Tortrix spp., Trichoplusia ni und Yponomeuta spp.; of the order of the Coleoptera, for example Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp. Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. und Trogoderma spp.; of the order of the Orthoptera, for example Blatta spp., Blattella spp., Gryllotalpa spp., *Leucophaea maderae*, Locusta spp., Periplaneta spp. and Schistocerca spp.; of the order of the Isoptera, for example Reticulitermes spp.; of the order of the Psocoptera, for example Liposcelis spp.; of the order of the Anoplura, for example Haematopinus spp., Linognathus spp. Pediculus spp., Pemphigus spp. and Phylloxera spp.; of the order of the Mallophaga, for example Damalinea spp. and Trichodectes spp.; of the order of the Thysanoptera, for example Frankliniella spp., Hercinothrips spp., Taeniothrips spp., *Thrips palmi, Thrips tabaci* and *Scirtothrips aurantii*; of the order of the Heteroptera, for example Cimex spp., *Distantiella theobroma*, Dysdercus spp., Euchistus spp. Eurygaster spp. Leptocorisa spp., Nezara spp., Piesma spp., Rhodnius spp., *Sahlbergella singularis*, Scotinophara spp. and Triatoma spp.; of the order of the Homoptera, for example *Aleurothrixus floccosus, Aleyrodes brassicae,* Aonidiella spp., Aphididae, Aphis spp., Aspidiotus spp., *Bemisia tabaci,* Ceroplaster spp., *Chrysomphalus aonidium, Chrysomphalus dictyospermi, Coccus hesperidum,* Empoasca spp., *Eriosoma larigerum,* Erythroneura spp., Gascardia spp., Laodelphax spp., *Lecanium corni,* Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica,* Quadraspidiotus spp., Rhopalosiphum spp., Saissetia spp., Schaphoideus spp., Schizaphis spp., Sitobion spp., *Trialeurodes vaporariorum, Trioza erytreae* and *Unaspis citri;* of the order of the Hymenoptera, for example Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.; of the order of the Diptera, for example Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp. Oscinella frit, *Pegomyia hyoscyami,* Phorbia spp., *Rhagoletis pomonella,* Sciara spp., Stomoxys spp., Tabanus spp., Tannia spp. and Tipula spp.; of the order of the Siphonaptera, for example Ceratophyllus spp., Xenopsylla cheopis; of the order of the Acarina, for example *Acarus siro, Aceria sheldoni, Aculus schlechtendali,* Amblyomma spp., Argas spp., Boophilus spp., Brevipalpus spp., *Bryobia praetiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Ornithodoros spp., Panonychus spp., *Phyllocoptruta oleivora, Polyphagotarsonemus latus,* Psoroptes spp., Rhipicephalus spp., Rhizoglyphus spp., Sarcoptes spp., Tarsonemus spp. and Tetranychus spp.; and of the order of the Thysanura, for example *Lepisma saccharina.*

The compounds of the invention have been found especially useful for controlling rice cicadas, for example of the families Delphicidae and Cicadellidae such as *Nilaparvata lugens, Laodelphax striatellus* and *Nephotettix cincticeps.* The compounds of formula I are also outstandingly effective against the so-called "white flies", which are very difficult to control, of the family Aleyrodidae, of the genera Bemisia and Trialeurodes such as *Bemisia tabaci* or *Trialeurodes vaporarium.* The compounds of formula I are very effective against fruit tree pests of the families Tortricidae and Olethreutidae, for example of the genera Cydia, Adoxophyes and Lobesia, with the species *Cydia pomonella, Adoxophyes orana* and *Lobesia botrana.* In the control of pests which are parasites of animals, especially of domestic animals and productive livestock, the principal pests are ectoparasites such as mites and ticks such as *Boophilus microplus* and *Dermanyssidae gallinae,* Diptera such as *Lucilia sericata,* and fleas such as *Ctenocephalides felis.*

In the target groups of the cited pests, the compounds of formula I substantially effect an inhibition of growth or development of the different development stages, so that the diminution of infestation by the pests is attributable to interference in the development of the pests, especially to a chemosterilising and ovicidal effect.

On account of their advantageous activity, compounds of formula I to be highlighted are those in which $R_1$ is $C_1-C_1$alkyl, $R_2$ is $C_1-C_4$alkyl, $C_1-C_4$alkoxy, $C_1-C_4$alkoxycarbonyl, di-($C_1-C_4$alkyl)amino or $-CONR_8R_9$, where $R_8$ is hydrogren or $C_1-C_4$alkyl, $R_9$ is hydrogen, $C_1-C_4$alkyl or phenyl, or $R_8$ and $R_9$ together are a $C_4-C_6$alkylene chain which may be interrupted by oxygen.

Among this group of preferred compounds, those compounds are in turn preferred in which $R_2$ is $C_1-C_4$alkyl, $C_1-C_4$alkoxy, $C_1-C_4$alkoxycarbonyl, di-($C_1-C_4$alkyl)carbamoyl or $C_4-C_6$alkylenecarbamoyl.

A particularly preferred group of compounds of formula I comprises those wherein $R_1$ is $C_1-C_4$alkyl, $R_2$ is $C_1-C_4$alkyl, $C_1-C_4$alkoxy, di-($C_1-C_2$alkyl)carbamoyl or $C_1-C_4$alkoxycarbonyl, $R_3$ is methyl and $R_4$ is hydrogen.

Preferred individual compounds of this invention are:

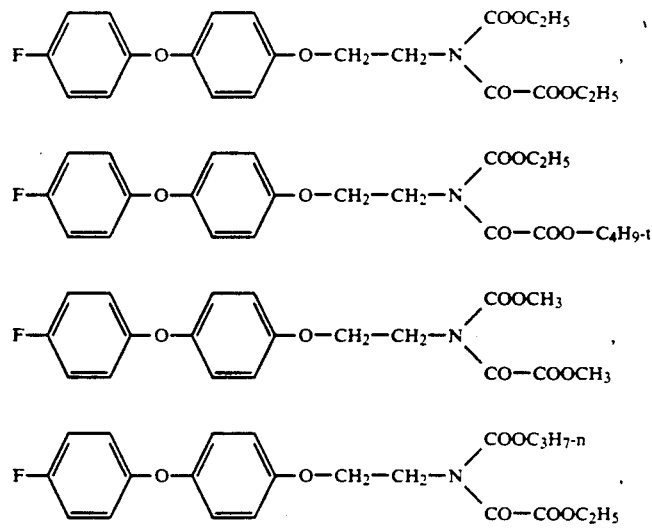

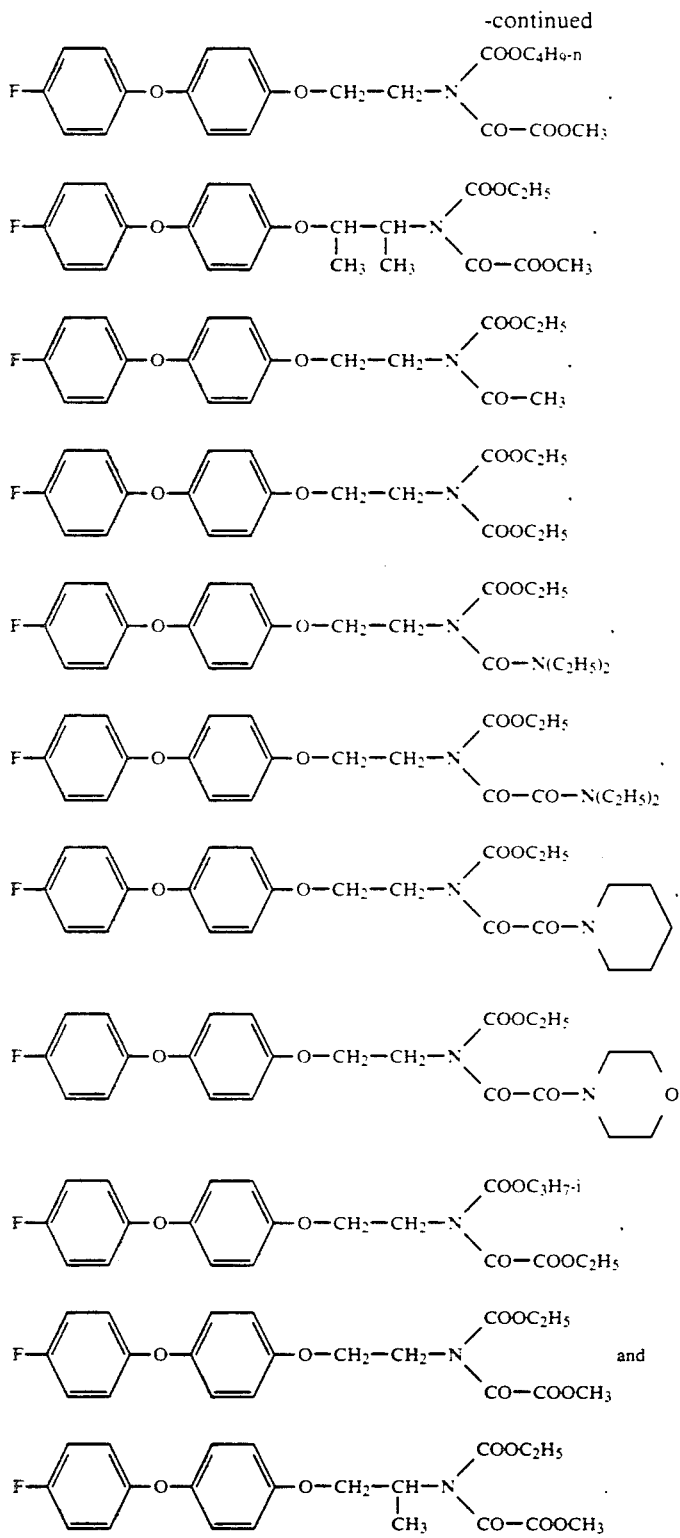
The compounds of formula I can be prepared by methods which are known per se. Thus, for example, the compounds of formula I can be prepared by acylating a fluorophenoxyphenoxyethylcarbamate of formula II
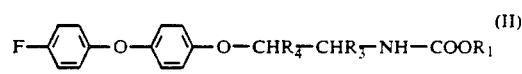
wherein $R_1$, $R_3$ and $R_4$ are as defined for formula I, with an activated acyl compound of formula III
$$X-CO-R_2 \qquad (III)$$

wherein $R_2$ is as defined for formula I and X is chloro; bromo, $-O-CO-R_2$ or $-O-CO(C_1-C_4\text{alkyl})$.

The process of the invention is preferably carried out in the presence of a base. Suitable bases are inorganic bases such as alkali metal and alkaline earth metal carbonates and hydrogencarbonates, for example sodium carbonate, potassium carbonate, sodium hydrogencarbonate or potassium hydrogencarbonate, or alkali metal or alkaline earth metal hydrides such as sodium hydride or calcium hydride, as well as organic bases such as tertiary amines, for example trialkylamines such as triethylamine, diisopropylethylamine, pyridine, dimethylaminopyridine, 1,4-diazabicyclo[2,2,2]octane or 1,8-diazabicyclo[5,4,0]undec-7-ene, alkali metal alcoholates such as sodium methylate, sodium ethylate or potassium tert-butylate, or alkali metal alkyl compounds such as butyllithium.

The reactions for the preparation of the compounds of formula I are carried out conveniently in inert, aprotic organic solvents. Such solvents are hydrocarbons such as hexane, heptane, cyclohexane, ligroin, benzene, toluene, xylene, mesitylene or tetraline; chlorinated hydrocarbons such as dichlormethane, chloroform, carbon tetrachloride, chlorobenzene, dichlorobenzene, trichloroethane or tetrachloroethane; ethers such as diethyl ether, 1,2-dimethoxy ether, tetrahydrofuran or dioxane; nitriles such as acetonitrile or propionitrile; dimethyl sulfoxide or sulfolane; or dialkylformamides such as dimethyl formamide or dimethyl acetamide.

Depending on the choice of solvent and the base to be optionally used, the reaction temperatures of the process of the invention are ordinarily in the range from $-10°$ C. to the boiling point of the reaction mixture, usually from $0°$ to $+130°$ C. The preferred temperature range is from $+20°$ to $+100°$ C. When using very reactive reagents, for example butyllithium, the reaction temperature will preferably be kept substantially lower, from ca. $-80°$ C. to $+20°$ C. The preferred range here is from $-70°$ to $0°$ C.

Aside from the process for the preparation of the compounds of formula I by reacting II with III, it has been found useful when preparing the compounds of formula I, wherein $R_2$ is the group $-CO-R_5$, to react the compound of formula II first in an inert solvent with oxalyl chloride, and to react the intermediate of formula

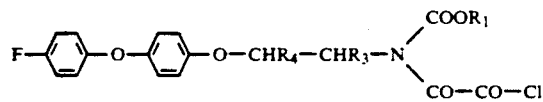

wherein $R_1$, $R_3$ and $R_4$ are as defined for formula I, in the presence of a base, with an alcohol or an amine of formula $$H-R_5$$

wherein $R_5$ is as defined for formula I.

Most of the starting materials of formulae II and III are known. Novel individual compounds which fall under formulae II and III can be prepared by known methods. Thus the starting materials of formula II are obtained in simple manner by reacting a 2-[4-(4-fluopophenoxy)phenoxy]ethylamine of formula IV

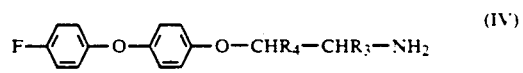

wherein $R_3$ and $R_4$ are as defined for formula I, with a haloformate of formula V $$\text{Hal}-CO-OR_1 \qquad (V)$$

wherein $R_1$ is as defined for formula I and Hal is halogen, preferably bromo or chloro, in the presence of a base.

The compounds of formula II can also be obtained by reacting 4-(4-fluorophenoxy)phenol with a 2-haloethylcarbamate $X-CHR_4-CHR_3-NH-COOR_1$ (X=Cl, Br), in the presence of a base.

The compounds of formulae IV and V are known, except for the individual compounds 2-[4-(4-fluorophenoxy)phenoxy]-1-methylethylamine (compound IVa) and 2-[4-(4-fluorophenoxy)phenoxy]-1-methylpropylamine (compound IVb). These novel intermediates can be prepared in the following manner by "reductive amination":

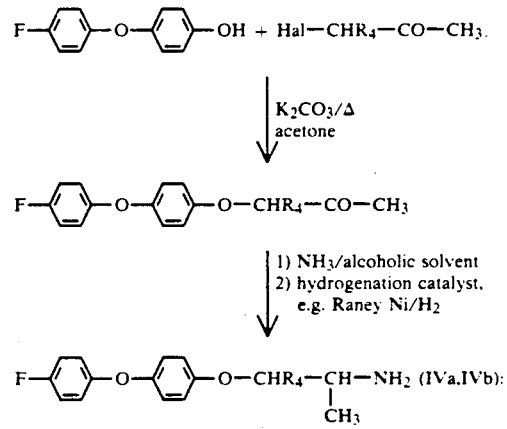

Hal is chloro or bromo. $R_4$ is hydrogen or methyl. The compounds IVa and IVb are novel and, together with the process for their preparation, also constitute an object of the invention.

The activity of the compounds of this invention and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formula I can also be used with particular advantage with substances which exert a pesticidally potentiating effect. Such compounds include, for example: piperonyl butoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioate.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$-$C_{22}$-alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphated adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyl bis(2-chloroethyl)ethylammonium bromide.

The surfactants customarily employed in the art of formulation are described e.g. in the following publications:

"1985 International Mc Cutcheon's Emulsifiers & Detergents", Glen Rock NJ USA, 1985", H. Stache, "Tensid-Taschenbuch"(Handbook of Surfactants), 2nd.ed., C. Hanser Verlag Munich/Vienna 1981, M. and J. Ash, "Encyclopedia of Surfactants", Vol,I-III, Chemical Publishing Co., New York, 1980-1981.

The pesticidal compositions usually contain 0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration. Typical rates of concentration are from 0.1 to 1000 ppm, preferably from 0.1 to 500 ppm. The rates of application per hectare are in general from 10 to 1000 g per hectare, preferably from 25 to 250 g/ha.

Preferred formulations are composed in particular of the following constituents (%=percentage by weight):

| Emulsifiable concentrates | |
|---|---|
| pesticide | 1 to 50%, preferably 5 to 30% |
| surfactant | 5 to 30%, preferably 10 to 20% |
| liquid carrier | 20 to 94%, preferably 50 to 85% |
| Dusts | |
| pesticide | 0.1 to 10%, preferably 0.1 to 1% |
| solid carrier | 99.9 to 90%, preferably 99.9 to 99% |
| Suspension concentrates | |
| pesticide | 5 to 75%, preferably 10 to 50% |
| water | 94 to 25%, preferably 90 to 30% |
| surfactant | 1 to 40%, preferably 2 to 30% |
| Wettable powders | |
| pesticide | 0.5 to 90%, preferably 1 to 80% |
| surfactant | 0.5 to 20%, preferably 1 to 15% |
| solid carrier | 5 to 95%, preferably 15 to 90% |
| Granulates | |
| pesticide | 0.5 to 30%, preferably 3 to 15% |
| solid carrier | 99.5 to 70%, preferably 97 to 85% |

The compositions can also contain further ingredients such as antifoams, preservatives, viscosity regulators, binders, tackifiers and fertilisers or other chemical agents to obtain special effects.

The invention is illustrated by the following non-limitative Examples.

EXAMPLE P1

Ethyl N-methoxalyl-2-[4-(4-fluorophenoxy)phenoxy]ethylcarbamate

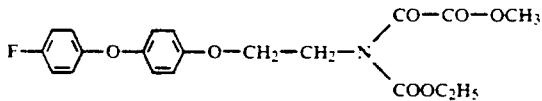

With stirring and under nitrogen, a solution of methoxalyl chloride in 10 ml of 1,2-dichloroethane is added dropwise at +80° C. over 20 minutes to a solution of 10.0 g of ethyl 2-[4-(4-fluorophenoxy)phenoxy]ethylcarbamate and 0.3 g of 4-dimethylaminopyridine in 70 ml of 1,2-dichloroethane. The mixture is then stirred for 16 hours at +80° C. After cooling to room temperature, the reaction mixture is washed in succession with a cold 5% solution of sodium hydrogencarbonate, with 0.1N hydrochloric acid and, finally, with water, and dried over sodium sulfate. The 1,2-dichloroethane is completely removed by vacuum distillation. If desired, the crude ethyl N-methoxalyl-2-[4-(4-fluorophenoxy)-phenoxy]ethylcarbamate can be purified by chromatography (eluant: 5:1 mixture of n-hexane/diethyl ether); $n_D^{20}$: 1.5295.

In similar manner, the following compounds of the invention are obtained from ethyl 2-[4-(4-fluorophenoxy)phenoxy]ethylcarbamate and methoxalyl chloride or tert-butoxalyl chloride:

ethyl N-ethoxalyl-2-[4-(4-fluorophenoxy)phenoxy]ethylcarbamate, $n_D^{20}$: 1.5285, and ethyl N-tert-butoxalyl-2-[4-(4-fluorophenoxy)phenoxy]ethylcarbamate $n_D^{20}$: 1.5200.

EXAMPLE P2

Ethyl N-methoxalyl-2-[4-(4-fluorophenoxy)phenoxy]-1-methylethylcarbamate

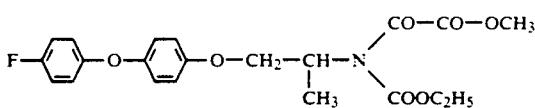

a) 1-[4-(4-fluorophenoxy)phenoxy]-2-propanone.

83 g of pulverised potassium carbonate and 4 g of of finely powdered potassium iodide are added to a solution of 94.1 g of 4-(4-fluorophenoxy)phenol in 400 ml of methyl ethyl ketone, and the mixture is heated to reflux temperature. With stirring, 64 g of freshly distilled chloroacetone are added dropwise over 1 hour, and the reaction mixture is stirred for a further 2 hours at reflux temperature. After cooling, the reaction mixture is filtered and the solvent is removed by vacuum distillation. The crude product is recrystallised from n-hexane/diethyl ether (5:1), to give the pure, colourless 1-[4-(4-fluorophenoxy)phenoxy]-2-propanone which melts at 56°-57° C.

b) 2-Amino-1-[4-(4-Fluorophenoxy)phenoxy]-2-propane.

26 g of 1-[4-(4-fluorophenoxy)phenoxy]-2-propanone are dissolved in an autoclave in 250 ml of methanol and to the solution are added 2.4 g of Raney nickel. Then 17 g of liquid ammonia are run in and hydrogen is blown in under pressure. The reaction mixture is hydrogenated at 50 bar and +40° C. for 11 hours. Then a further 2.4 g of Raney nickel and 17 g of ammonia are added and hydrogenation is carried out for a further 9 hours at +40° C. and 50 bar hydrogen pressure until complete conversion of the educt. The reaction mixture is filtered, and the solvent is completely removed by vacuum distillation. The crude product is chromatographed over silica gel (eluant: 9:1 mixture of diethyl ether/methanol), to give the pure 2-amino-1-[4-(4-fluorophenoxy)phenoxy]-2-propane as a colourless oily liquid with the refractive index $n_D^{20}$: 1.5531.

c) Ethyl 2-[4-(4-fluorophenoxy)phenoxy]-1-methylethylcarbamate.

With stirring, a solution of 5.9 g of ethyl chloroformate in 10 ml of toluene is added dropwise at 20°-22° C. over 30 minutes to a solution of 13.1 g of 2-amino-1-[4-(4-fluorophenoxy)phenoxy]-2-propane, 9.5 g of diisopropylethylamine and 0.4 g of 4-dimethylaminopyridine in 70 ml of toluene. The reaction mixture is subsequently stirred for 15 hours at room temperature. For working up, the reaction mixture is poured into 300 ml of ice-water and extracted three times with ether. The combined organic extracts are washed twice with 0.2N hydrochloric acid and with water. The organic solution is dried over sodium sulfate and the solvent is removed by distillation. The crude product is purified by chromatography over silica gel (eluant: 2:1 mixture of n-hexane/diethyl ether), to give the pure ethyl 2-[4-(4-fluorophenoxy)phenoxy]-1-methylethylcarbamate in the form of colourless crystals with a melting point of 55°-56° C.

d) Ethyl N-methoxalyl-2-[4-(4-fluorophenoxy)phenoxy]-1-methylethylcarbamate. With stirring and under nitrogen, a solution of 11.8 g of methoxalyl chloride in 10 ml of 1,2-dichloroethane is added dropwise at +80° C. over 20 minutes to a solution of 8.0 g of ethyl 2-[4-(4-fluorophenoxy)phenoxy]-1-methylethylcarbamate and 0.3 g of 4-dimethylaminopyridine in 50 ml of 1,2-dichloroethane. The mixture is thereafter stirred for 16 hours at +80° C. After cooling to room temperature, the reaction mixture is washed in succession with a cold 5% solution of sodium hydrogencarbonate, then with 0.1N hydrochloric acid and, finally, with water. The 1,2-dichloromethane is completely removed by vacuum distillation. If desired, the ethyl N-methoxalyl-2-[4-(4-fluorophenoxy)phenoxy]-1-methylethylcarbamate can be purified over silica gel 60 (eluant: 2:1 mixture of n-hexane/dichloromethane): $n_D^{24}$: 1.5230.

EXAMPLE P3

Ethyl N-methoxalyl-2-[4-(4-fluorophenoxy)phenoxy]-1-methyl-propylcarbamate

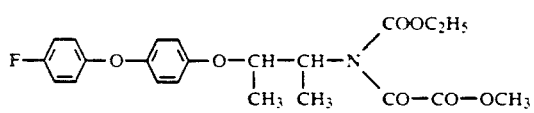

In accordance with the procedure described in Example P2, the intermediate 2-[4-(4-fluorophenoxy)-phenoxy]-3-butanone, $n_D^{20}$ 1.5412, is obtained from 4-(4-fluorophenoxy)phenol and 2-chloro-3-butanone;

b) the intermediate 2-[4-(4-fluorophenoxy)phenoxy]-3-aminobutane, $n_D^{20}$:1.5485, is obtained from 2-[4-(4-fluorophenoxy)phenoxy]-3-butanone and ammonia in the presence of Raney nickel;

c) the intermediate ethyl 2-[4-(4-fluorophenoxy)-phenoxy]-1-methylpropylcarbamate, $n_D^{20}$:1.5331, is obtained from 2-[4-(4-fluorophenoxy)phenoxy]-3-aminobutane and ethyl chloroformate;

d) ethyl N-methoxalyl-2-[4-(4-fluorophenoxy)-phenoxy]-1-methylethylcarbamate, $n_D^{21}$:1.5201, is obtained from ethyl 2-[4-(4-fluorophenoxy)phenoxy]-1-methylpropylcarbamate and methoxalyl chloride.

EXAMPLE P4

Methyl N-methoxalyl-2-[4-(4-fluorophenoxy)-phenoxy]ethylcarbamate

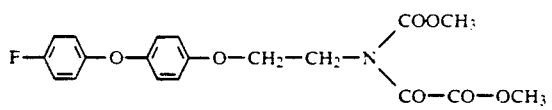

a) 3.6 g of powdered potassium carbonate, 1.5 g of finely powdered potassium iodide and 27 g of methyl 2-chloroethylcarbamate are added to a solution of 2.6 g of 4-(4-fluorophenoxy)phenol in 120 ml of dimethyl formamide, and the reaction mixture is heated for 15 hours to 95° C. The cooled reaction mixture is poured into ice-water and extracted repeatedly with ether. The combined ether phases are washed with water, dried over sodium sulfate, and the solvent is completely removed by distillation. After filtration over silica gel, the crude product is recrystallised from diethyl ether/hexane to give methyl 2-[4-(4-fluorophenoxy)phenoxy]-1-ethylcarbamate with a melting point of 64°-66° C.

The following alkylcarbamates are prepared in analogous manner from the n-propyl, isopropyl and n-butyl esters of 2-chloroethylcarbamic acid and 4-(4-fluorophenoxy)-phenol:

n-propyl 2-[4-(4-fluorophenoxy)phenoxy]-1-ethylcarbamate, m.p. 73°-74° C.

isopropyl 2-[4-(4-fluorophenoxy)phenoxy]-1-ethylcarbamate, m.p. 72°-74° C.

n-butyl 2-[4-(4-fluorophenoxy)phenoxy]-1-ethylcarbamate, m.p. 63°-64° C.

b) Following the procedure of Example P1, the following alkyl esters of N-alkoxalyl-2-[4-(4-fluorophenoxy)phenoxy]ethylcarbamic acid are prepared from the alkylcarbamates obtained in a) by reaction with methoxalyl chloride:

methyl N-methoxalyl-2-[4-(4-fluorophenoxy)phenoxy]ethylcarbamate, $n_D^{20}$:1.5377;

n-propyl N-ethoxalyl-2-[4-(4-fluorophenoxy)phenoxy]ethylcarbamate, $n_D^{20}$:1.5249;

isopropyl N-methoxalyl-2-[4-(4-fluorophenoxy)phenoxy]ethylcarbamate, $n_D^{20}$:1.5226;

n-butyl N-methoxalyl-2-[4-(4-fluorophenoxy)phenoxy]ethylcarbamate, $n_D^{20}$:1.5267.

EXAMPLE P5

Ethyl N-ethoxycarbonyl-2-[4-(4-fluorophenoxy)-phenoxy]ethylcarbamate

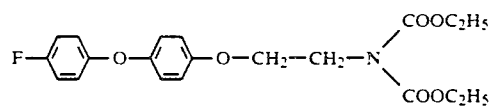

1.56 g of a 55% dispersion of sodium hydride in mineral oil are washed repeatedly with n-hexane and suspended in 30 ml of tetrahydrofuran. With stirring, a solution of 11.4 g of ethyl 2-[4-(4-fluorophenoxy)-phenoxy]ethylcarbamate in 30 ml of tetrahydrofuran is added dropwise at room temperature to the above suspension, and the reaction mixture is stirred for a further 4 hours at room temperature until the sodium hydride is completely reacted. Then a solution of 4.7 g of freshly distilled ethyl chloroformate in 10 ml of tetrahydrofuran is added dropwise at 0°-5° C. over 10 minutes, and the mixture is stirred for a further 50 minutes at room temperature. The reaction mixture is poured into ice-water and extracted repeatedly with ether. The combined ether phases are washed twice with a cold saturated solution of sodium hydrogencarbonate, then with water and a solution of sodium chloride. The organic phase is dried over sodium sulfate and the solvent is removed by distillation. The crude product is further purified by chromatography over silica gel (eluant: 5:1 mixture of n-hexane/diethyl ether), to give ethyl N-ethoxycarbonyl-2-[4-(4-fluorophenoxy)phenoxy]ethylcarbamate as a colourless viscous oil; $n_D^{23}$:1.5257.

The following compounds are prepared in analogous manner:

ethyl N-acetyl-2-[4-(4-fluorophenoxy)phenoxy]ethylcarbamate, m.p. 52°-53° C., from ethyl 2-[4-(4-fluorophenoxy)phenoxy]ethylcarbamate and acetyl chloride, and ethyl N-diethylcarbamoyl-2-[4-(4-fluorophenoxy)-phenoxy]ethylcarbamate, $n_D^{20}$:1.5318, from ethyl 2-[4-(4-fluorophenoxy)phenoxy]ethylcarbamate and freshly distilled diethylcarbamoyl chloride.

EXAMPLE P6

Ethyl N-(N-morpholinoxalyl)-2-[4-(4-fluorophenoxy)phenoxy]ethylcarbamate

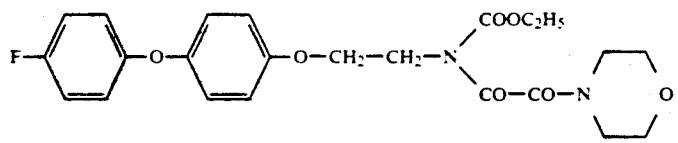

a) With stirring, 25.4 g of oxalyl chloride are added dropwise at room temperature to a solution of 30.5 g of ethyl 2-[4-(4-fluorophenoxy)phenoxy]ethylcarbamate in 100 ml of 1,2-dichloroethane, and the reaction mixture is heated for 3 hours to reflux temperature until no more gaseous hydrogen chloride evolves. The solvent and excess oxalyl chloride are then removed by distillation under nitrogen, and the resultant ethyl N-chloroxalyl-2-[4-(4-fluorophenoxy)phenoxy]ethylcarbamate is recrystallised from n-pentane to give colourless crystals with a melting point of 48°-50° C.

b) With stirring, a solution of 5.2 g of morpholine in 20 ml of toluene is added dropwise at 0°-5° C. over 30 minutes to a solution of ethyl N-chloroxalyl-2-[4-(4-fluorophenoxy)phenoxy]ethylcarbamate in 80 ml of toluene. The reaction mixture is subsequently stirred for 2 hours at room temperature. The reaction mixture is then washed in succession with ice-cold 1N hydrochloric acid, with a 10% solution of sodium hydrogencarbonate and with water, and dried over sodium sulfate.

The solvent is completely removed by distillation and, finally, the colourless, viscous ethyl N-(N-morpholinoxalyl)-2-[4-(4-fluorophenoxy)phenoxy]ethylcarbamate is completely degassed under a high vacuum; $n_D^{21}$:1.5471.

The following compounds are prepared in analogous manner from ethyl N-chloroxalyl-2-[4-(4-fluorophenoxy)phenoxy]ethylcarbamate and piperidine or diethylamine:

ethyl N-(N-piperidinoxalyl)-2-[4-(4-fluorophenoxy)phenoxy]ethylcarbamate, $n_D^{21}$:1.5451, and ethyl N-(N-diethylaminoxalyl)-2-[4-(4-fluorophenoxy)phenoxy]ethylcarbamate, $n_D^{21}$:1.5349.

The following compounds of formula I can be prepared in analogous manner:

TABLE 1

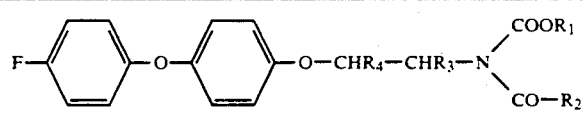

| Comp. | $R_1$ | $R_2$ | $R_3$ | $R_4$ | Physical data |
|---|---|---|---|---|---|
| 1.01 | $C_2H_5$ | $COOC_2H_5$ | H | H | $n_D^{21}$: 1.5285 |
| 1.02 | $C_2H_5$ | $COOC_4H_{9}$-t | H | H | $n_D^{21}$: 1.5200 |
| 1.03 | $C_2H_5$ | $COOCH_3$ | H | H | $n_D^{20}$: 1.5295 |
| 1.04 | $C_2H_5$ | $COOC_2H_5$ | $CH_3$ | H | |
| 1.05 | $CH_3$ | $COOCH_3$ | H | H | $n_D^{20}$: 1.5377 |
| 1.06 | $C_3H_7$-n | $COOC_2H_5$ | H | H | $n_D^{20}$: 1.5249 |
| 1.07 | $C_4H_9$-n | $COOCH_3$ | H | H | $n_D^{20}$: 1.5267 |
| 1.08 | $C_2H_5$ | $COOCH_3$ | $CH_3$ | H | $n_D^{24}$: 1.5230 |
| 1.09 | $C_2H_5$ | $COOCH_3$ | $CH_3$ | $CH_3$ | $n_D^{21}$: 1.5201 |
| 1.10 | $C_2H_5$ | $CH_3$ | H | H | m.p. 52-53° C. |
| 1.11 | $C_2H_5$ | $C_3H_7$-n | H | H | |
| 1.12 | $C_2H_5$ | $OC_2H_5$ | H | H | $n_D^{23}$: 1.5257 |
| 1.13 | $C_2H_5$ | $OCH_3$ | H | H | |
| 1.14 | $C_2H_5$ | $OC_4H_9$-n | H | H | |
| 1.15 | $C_2H_5$ | $COOC_8H_{17}$-n | H | H | |
| 1.16 | $C_2H_5$ | $COOC_3H_7$-i | H | H | |
| 1.17 | $C_2H_5$ | $-N(CH_3)_2$ | H | H | |
| 1.18 | $C_2H_5$ | $-N(C_2H_5)_2$ | H | H | $n_D^{20}$: 1.5318 |
| 1.19 | $C_2H_5$ | $CO-N(C_2H_5)_2$ | H | H | $n_D^{20}$: 1.5349 |
| 1.20 | $C_2H_5$ | CO-N(piperidinyl) | H | H | $n_D^{21}$: 1.5451 |
| 1.21 | $C_2H_5$ | $CO-N(C_4H_9-n)_2$ | H | H | |
| 1.22 | $C_2H_5$ | $CO-NHC_4H_9$-n | H | H | |
| 1.23 | $C_2H_5$ | $CO-NH-CH_2-C_6H_5$ | H | H | |
| 1.24 | $C_2H_5$ | CO-N(morpholinyl) | H | H | $n_D^{21}$: 1.5471 |
| 1.25 | $C_2H_5$ | $CO-N(CH_3)-C_6H_5$ | H | H | |
| 1.26 | $C_2H_5$ | $CO-NH-C_6H_5$ | H | H | |

TABLE 1-continued

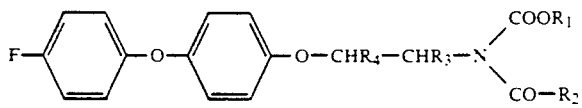

| Comp. | $R_1$ | $R_2$ | $R_3$ | $R_4$ | Physical data |
|---|---|---|---|---|---|
| 1.27 | $C_3H_7$-i | $COOC_2H_5$ | H | H | $n_D^{20}$: 1.5226 |

Formulation Examples for liquid compounds of formula I (throughout, percentages are by weight)

| F1. Emulsifiable concentrates | a) | b) | c) |
|---|---|---|---|
| compound 1.08 or 1.02 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| F2. Solutions | a) | b) | c) | d) |
|---|---|---|---|---|
| compound 1.02 | 80% | 10% | 5% | 95% |
| ethylene glycol monomethyl ether | 20% | — | — | — |
| polyethylene glycol 400 | — | 70% | — | — |
| N-methyl-2-pyrrolidone | — | 20% | — | — |
| epoxidised coconut oil | — | — | 1% | 5% |
| ligroin (boiling range 160-190°) | — | — | 94% | — |

These solutions are suitable for application in the form of microdrops.

| F3. Granulates | a) | b) |
|---|---|---|
| compound 1.03 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently removed by evaporation under vacuum.

| F4. Dusts | a) | b) |
|---|---|---|
| compound 1.01 | 2% | 5% |
| highly dispersed silicic acid | 1% | 5% |
| talcum | 97% | — |
| kaolin | — | 90% |

Ready for use dusts are obtained by intimately mixing the carriers with the active ingredient.

Formulation Examples for solid compounds of formula I (throughout, percentages are by weight)

| F5. Wettable powders | a) | b) | c) |
|---|---|---|---|
| compound 1.10 | 25% | 50% | 75% |
| sodium ligninsulfonate | 5% | 5% | — |
| sodium laurylsulfonate | 3% | — | 5% |
| sodium diisobutylnaphthalenesulfonate | — | 6% | 10% |
| octylphenol polyethylene glycol ether (7-8 mol of ethylene oxide) | — | 2% | — |
| highly dispersed silicic acid | 1% | 10% | 10% |
| kaolin | 62% | 27% | — |

The active ingredient is thouroughly mixed with the adjuvants and the mixture is thoroughly ground in a suitable mill, affording wettable powders which can be diluted with water to give suspensions of any desired concentration.

| F6. Emulsifiable concentrate | |
|---|---|
| compound 1.10 | 10% |
| octylphenol polyethylene glycol ether (4-5 mol of ethylene oxide) | 3% |
| calcium dodecylbenzene sulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

| F7. Dusts | a) | b) |
|---|---|---|
| compound 1.10 | 5% | 8% |
| talcum | 95% | — |
| kaolin | — | 92% |

Ready for use dusts are obtained by mixing the active ingredient with the carrier, and grinding the mixture in a suitable mill.

| F8. Extruder granulate | |
|---|---|
| compound 1.10 | 10% |
| sodium ligninsulfonate | 2% |
| carboxymethyl cellulose | 1% |
| kaolin | 87% |

The active ingredient is mixed and ground with the adjuvants, and the mixture is subsequently moistened with water. The mixture is extruded, granulated and then dried in a stream of air.

| F9. Coated granulate | |
|---|---|
| compound 1.10 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| F10 Suspension concentrate | |
| --- | --- |
| compound 1.10 | 40% |
| ethylene glycol | 10% |
| nonylphenol polyethylene glycol ether (15 mol of ethylene oxide) | 6% |
| sodium ligninsulfonate | 10% |
| 37% aqueous formaldehyde solution | 0.2% |
| silicone oil in the form of a 75% aqueous emulsion | 0.8% |
| water | 32% |

The finely ground active ingredient is homogeneously mixed with the adjuvants, giving a suspension concentrate from which suspensions of any desired concentration can be obtained by dilution with water.

In the following Biological Examples, good action means that the desired effect is at least 50-60%.

EXAMPLE B1

Action against *Boophilus microplus*

Replete adult females are fixed with adhesive tape to a PVC sheet and covered with a cotton wool swab. The test organisms are then treated by impregnating the cotton wool swab with 10 ml of an aqueous solution containing the test compound in a concentration of 125 ppm. The cotton wool swab is then removed and the ticks are incubated for 4 weeks for oviposition. The action against *Moophilus microplus* is observed either as kill or sterility of the females or takes the form of ovicidal action against the eggs.

In this test, compounds of Table 1 exhibit good action against Boophilus. In particular, compounds 1.01, 1.02, 1.03, 1.08, 1.10 and 1.12 are more than 80% effective.

EXAMPLE B2

Ovicidal action against *Cydia pomonella*

Eggs of *Cydia pomonella* laid on filter paper are immersed for a brief time in an aqueous acetonic solution containing the test compound in a concentration of 400 ppm. After the test solution has dried, the eggs are incubated in petri dishes. The percentage hatching rate of the eggs compared with untreated controls is determined 6 days later (percentage reduction of hatching).

In this test, compounds of Table 1 exhibit good action against *Cydia pomonella*.

EXAMPLE B3

Action against *Dermanyssus gallinae*

2 to 3 ml of a solution containing 10 ppm of test compound and ca. 200 mites in different development stages are put into a glass container which is open at the top. The container is then sealed with cotton wool, shaken for 10 minutes until the mites are thoroughly wetted, and then briefly held upside down so that the remainder of the test solution can be absorbed by the cotton wool. A mortality count is made after 3 days and the result expressed in percent.

Compounds of Table 1 exhibit good action against *Dermanyssus gallinae*.

EXAMPLE B4

Ovicidal action against *Adoxophyes reticulana*

Eggs of *Adoxophyes reticulana* laid on filter paper are immersed for a brief time in an aqueous acetonic solution containing the test compound in a concentration of 400 ppm. After the test solution has dried, the eggs are incubated in petri dishes. The percentage hatching rate of the eggs compared with untreated controls is determined 6 days later (percentage reduction of hatching).

In this test, compounds of Table 1 exhibit good action against *Adoxophyes reticulana*. In particular, compounds 1.01 and 1.02 are still more than 90% effective even at a concentration of 12.5 ppm.

EXAMPLE B5

Ovicidal action against *Lobesia botrana*

Eggs of *Lobesia botrana* deposited on filter paper are immersed for a brief time in an aqueous acetonic solution containing the test compound in a concentration of 400 ppm. After the test solution has dried, the eggs are incubated in petri dishes. The percentage hatching rate of the eggs compared with untreated controls is determined 6 days later (percentage reduction of hatching).

In this test, compounds of Table 1 exhibit good action against *Lobesia botrana* In particular, compounds 1.01 and 1.02 are still more than 90% effective even at a concentration of 12.5 ppm.

EXAMPLE B6

Action against *Aonidiella aurantii*

Small potato tubers are populated with *Aonidiella aurantii* crawlers (California red scale). After ca. 2 weeks, the potatoes are immersed in a spray mixture prepared from an aqueous emulsion or suspension containing the test compound in a concentration of 400 ppm. After the treated potato tubers have dried, they are incubated in plastic containers. Evaluation is made 10-12 weeks later by comparing the survival rate of the crawlers of the first filial generation of the treated population with that of the untreated controls.

In this test, compounds of Table 1 exhibit good action against *Aonidiella aurantii*.

EXAMPLE B7

Chemosterilisation effect on *Nilaparvata lugens*

The test is carried out with growing plants. Four rice plants (thickness of the stem 8 mm, height ca. 20 cm) are each planted in pots having a diameter of 8 cm. The plants are sprayed to drip point with an aqueous emulsion formulation containing the test compound in a concentration of 400 ppm. After the spray coating has dried, each plant is populated with freshly hatched females and males of Nilaparvata. To prevent the test organisms from escaping, a glass cylinder is slipped over each of the plants and sealed with a gauze top. The adults remain for 5 days on the treated plant for oviposition and are then removed. The rice plants with the deposited eggs are then incubated for 14 days at +28° C., 70% relative humidity and a 14 hour light exposure (10 000 lux). The young nymphs which have hatched during this period ($F_1$ generation) are counted. The percentage reduction of the progeny (chemosterilisation effect=% age action) is determined by comparing the number of hatched nymphs on the treated plants with those hatched on the untreated control plants.

The compounds of Table 1 exhibit good activity in the above test. Compounds 1.01 and 1.02 are 100% effective at concentrations of 6 ppm, and are still 95% effective at a concentration of 1,.5 ppm.

EXAMPLE B8

Population-inhibiting effect on *Nephotettix cincticeps*

The test is carried out with growing rice plants. Twenty rice plants (thickness of the stem 1 mm, height ca. 20 cm) are each planted in porcelain pots having a diameter of 8 cm. The plants are sprayed to drip point with an aqueous emulsion formulation containing the test compound in a concentration of 400 ppm. After the spray coating has dried, each plant is populated with freshly hatched females and males of Nephotettix. To prevent the test organisms from escaping, a plexiglass cylinder is slipped over each of the plants and sealed with a gauze top. The adults remain for 5 days on the treated plant for oviposition and are then removed. The rice plants with the deposited eggs are then incubated for 14 days at +28° C., 70% relative humidity and a 14 hour light exposure (10 000 lux). The young nymphs which have hatched during this period ($F_1$ generation) are counted. The percentage reduction of the progeny (percentage reduction in population) is determined by comparing the number of hatched nymphs on the treated plants with those hatched on the untreated control plants.

The compounds of Table 1 exhibit good activity in the above test.

EXAMPLE B9

Action against *Bemisia tabuci*

Dwarf beans are placed in gauze cages and populated with adults of *Bemisia tabaci* (white flies). After oviposition, all the adults are removed and 10 days later the plants with the nymphs present thereon are treated with an emulsion spray mixture containing the test compound in a concentration of 400 ppm. Evaluation of the hatching rate is made 14 days after application in comparison with untreated controls.

The compounds of Table exhibit good activity in this test. Compounds 1.01 and 1.02 are 100% effective at concentrations of 10 ppm.

What is claimed is:

1. A N-acyl-2-[4-(4-fluorophenoxy)phenoxy]ethyl-carbamate of formula I $$F-\text{C}_6\text{H}_4-\text{O}-\text{C}_6\text{H}_4-\text{O}-CHR_4-CHR_3-N(COOR_1)(CO-R_2) \quad (I)$$

wherein $R_1$ is $C_1$-$C_8$alkyl, $C_3$-$C_4$alkenyl or $C_3$-$C_4$alkynyl, $R_2$ is $C_1$-$C_8$alkyl, $C_1$-$C_8$alkoxy, —CO—$R_5$ or —$NR_6R_7$, $R_3$ and $R_4$ are each independently of the other hydrogen or methyl, $R_5$ is $C_1$-$C_8$alkoxy or —$NR_8R_9$, $R_6$ is $C_1$-$C_4$alkyl, $R_7$ is $C_1$-$C_4$alkyl, $R_8$ is hydrogen or $C_1$-$C_4$alkyl, and $R_9$ is hydrogen, $C_1$-$C_4$alkyl, benzyl, phenyl or phenyl which is substituted by halogen or methyl.

2. A compound according to claim 1, wherein $R_1$ is $C_1$-$C_1$alkyl, $R_2$ is $C_1$-$C_4$alkyl, $C_1$-$C_4$alkoxy, $C_1$-$C_4$alkoxycarbonyl, di-($C_1$-$C_4$alkyl)amino or —$CONR_8R_9$, where $R_8$ is $C_1$-$C_4$alkyl, $R_9$ is hydrogen or $C_1$-$C_4$alkyl.

3. A compound according to claim 2, wherein $R_2$ is $C_1$-$C_4$alkyl, $C_1$-$C_4$alkoxy, $C_1$-$C_4$alkoxycarbonyl, di-($C_1$-$C_4$alkyl)carbamoyl or $C_4$-$C_6$alkylenecarbamoyl.

4. A compound according to claim 1, wherein $R_1$ is $C_1$-$C_4$alkyl, $R_2$ is $C_1$-$C_4$alkyl, $C_1$-$C_4$alkoxy, $C_1$-$C_4$alkoxycarbonyl or di-($C_1$-$C_2$alkyl)carbamoyl, $R_3$ is methyl and $R_4$ is hydrogen.

5. A compound according to claim 1 selected from the group consisting of

F—C₆H₄—O—C₆H₄—O—CH₂—CH₂—N(COOC₂H₅)(CO—COOC₂H₅),

F—C₆H₄—O—C₆H₄—O—CH₂—CH₂—N(COOC₂H₅)(CO—COO—C₄H₉-t),

F—C₆H₄—O—C₆H₄—O—CH₂—CH₂—N(COOCH₃)(CO—COOCH₃),

F—C₆H₄—O—C₆H₄—O—CH₂—CH₂—N(COOC₃H₇-n)(CO—COOC₂H₅),

F—C₆H₄—O—C₆H₄—O—CH₂—CH₂—N(COOC₄H₉-n)(CO—COOCH₃).

-continued

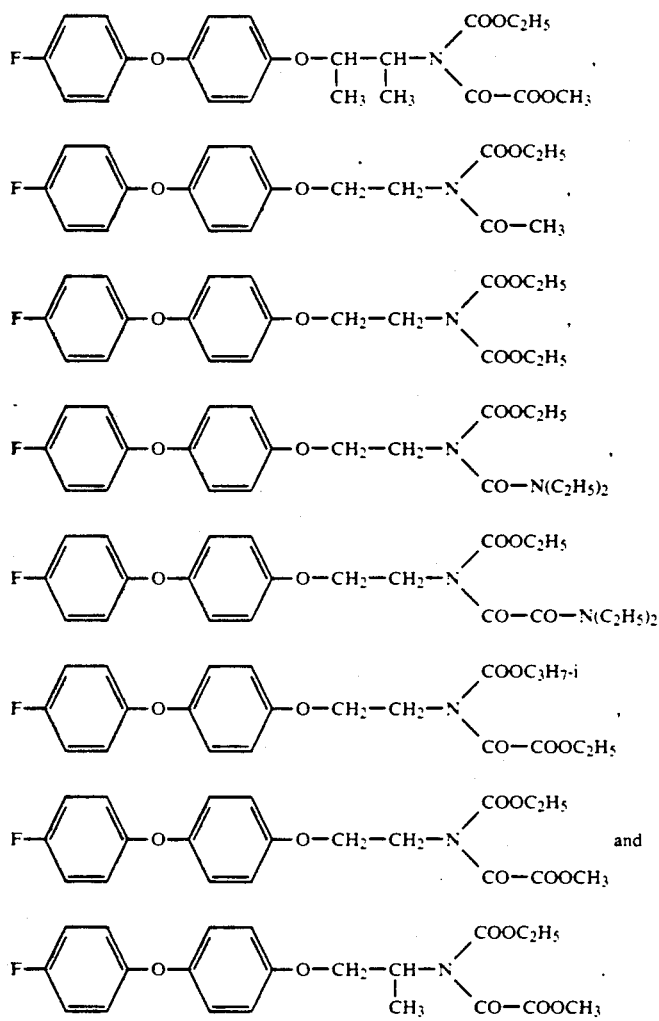

6. An insecticidal or arachnicidal composition wherein the active component comprises an effective amount of a compound of the formula

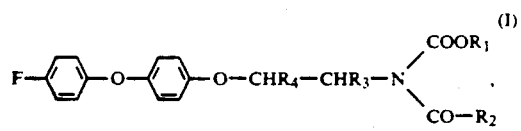

wherein
$R_1$ is $C_1$-$C_8$alkyl, $C_3$-$C_4$alkenyl or $C_3$-$C_4$alkynyl,
$R_2$ is $C_1$-$C_8$alkyl, $C_1$-$C_8$alkoxy, —CO—$R_5$ or —$NR_6R_7$,
$R_3$ and $R_4$ are each independently of the other hydrogen or methyl,
$R_5$ is $C_1$-$C_8$alkoxy or —$NR_8R_9$,
$R_6$ is $C_1$-$C_4$alkyl,
$R_7$ is $C_1$-$C_4$alkyl,
$R_8$ is hydrogen or $C_1$-$C_4$alkyl, and
$R_9$ is hydrogen, $C_1$-$C_4$alkyl, benzyl, phenyl or phenyl which is substituted by halogen or methyl, and an agrochemically acceptable adjuvant.

7. A method of controlling pests selected from insects and arachnids, which comprises contacting said pests with an insecticidally or arachnicidally effective amount of a compound of formula

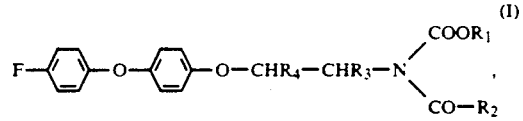

wherein
$R_1$ is $C_1$-$C_8$alkyl, $C_3$-$C_4$alkenyl or $C_3$-$C_4$alkynyl,
$R_2$ is $C_1$-$C_8$alkyl, $C_1$-$C_8$alkoxy, —CO—$R_5$ or —$NR_6R_7$,
$R_3$ and $R_4$ are each independently of the other hydrogen or methyl,
$R_5$ is $C_1$-$C_8$alkoxy or —$NR_8R_9$,
$R_6$ is $C_1$-$C_4$alkyl,
$R_7$ is $C_1$-$C_4$alkyl,
$R_8$ is hydrogen or $C_1$-$C_4$alkyl, and
$R_9$ is hydrogen, $C_1$-$C_4$alkyl, benzyl, phenyl or phenyl which is substituted by halogen or methyl.

8. A method according to claim 7, wherein the pests to be controlled are phytopathagous noxious insects and mites.

9. A method according to claim 7 of chemosterilising noxious insects and mites that feed on plants.

* * * * *